(12) United States Patent
Lanci et al.

(10) Patent No.: US 10,322,991 B2
(45) Date of Patent: Jun. 18, 2019

(54) SELECTIVE AEROBIC OXIDATION OF DIMETHYLBIPHENYLS

(71) Applicant: ExxonMobil Research and Engineering Company, Annandale, NJ (US)

(72) Inventors: Michael P. Lanci, Flemington, NJ (US); Joshua W. Allen, Branchburg, NJ (US); Jarid M. Metz, Doylestown, PA (US); Victor DeFlorio, Newton, NJ (US); Jihad M. Dakka, Whitehouse Station, NJ (US); Bryan A. Patel, Jersey City, NJ (US); Michael Salciccioli, Houston, TX (US); Michael W. Weber, Hosuton, TX (US); Stephen Zushma, Clinton, NJ (US)

(73) Assignee: EXXONMOBIL RESEARCH AND ENGINEERING COMPANY, Annandale, NJ (US)

(*) Notice: Subject to any disclaimer, the term of this patent is extended or adjusted under 35 U.S.C. 154(b) by 0 days.

(21) Appl. No.: 15/829,060

(22) Filed: Dec. 1, 2017

(65) Prior Publication Data
US 2018/0179138 A1    Jun. 28, 2018

Related U.S. Application Data

(60) Provisional application No. 62/437,892, filed on Dec. 22, 2016, provisional application No. 62/437,823, filed on Dec. 22, 2016.

(51) Int. Cl.
*B01J 31/04* (2006.01)
*C07C 25/13* (2006.01)
(Continued)

(52) U.S. Cl.
CPC ............ *C07C 57/30* (2013.01); *B01J 31/04* (2013.01); *C07C 25/13* (2013.01); *C07C 47/23* (2013.01);
(Continued)

(58) Field of Classification Search
CPC .......... C07C 57/30; C07C 25/13; C07C 51/16
(Continued)

(56) References Cited

U.S. PATENT DOCUMENTS 2,723,994 A * 11/1955 Haefele ................. C07C 51/265
562/412
3,660,477 A    5/1972 Otterbach et al.
(Continued)

FOREIGN PATENT DOCUMENTS

JP    07025817    * 1/1995
JP    7025817 A    1/1995
(Continued)

OTHER PUBLICATIONS

JP07025817 translation 1995 (Year: 1995).*
(Continued)

*Primary Examiner* — Deborah D Carr
(74) *Attorney, Agent, or Firm* — Kristina Okafor

(57) ABSTRACT

A process for selective oxidation of dimethyl-1,1'-biphenyl to form methyl-1,1'-biphenyl mono-carboxylic acid(s), comprising contacting a solution of dimethyl-1,1'-biphenyl in acetic acid solvent in the presence of a Co(II) acetate catalyst and air, and optionally adding a co-solvent, or adding sodium or potassium acetate, and oxidizing the dimethyl-1,1'-biphenyl under time and temperature conditions sufficient to form one or more methyl-1,1'-biphenyl mono-carboxylic acid(s). The mono-carboxylic acids are advantageously isolated and esterified to form biphenyl mono-esters for use as plasticizers.

34 Claims, 6 Drawing Sheets

(51) Int. Cl.
*C07C 47/23* (2006.01)
*C07C 51/16* (2006.01)
*C07C 57/30* (2006.01)
*C07C 67/05* (2006.01)
*C07C 67/08* (2006.01)
*C07C 51/265* (2006.01)
*C07C 63/331* (2006.01)
*C07C 63/333* (2006.01)

(52) U.S. Cl.
CPC ............ *C07C 51/16* (2013.01); *C07C 51/265* (2013.01); *C07C 67/05* (2013.01); *C07C 67/08* (2013.01)

(58) Field of Classification Search
USPC ........................................................ 562/407
See application file for complete search history.

(56) References Cited

U.S. PATENT DOCUMENTS

| | | | |
|---|---|---|---|
| 5,763,649 A | 6/1998 | Fukuhara | |
| 6,274,756 B1 | 8/2001 | Caers et al. | |
| 6,730,625 B1 | 5/2004 | Chang et al. | |
| 7,855,305 B2 | 12/2010 | Parker et al. | |
| 9,328,053 B2 | 5/2016 | Bai et al. | |
| 9,580,572 B2 | 2/2017 | Dakka et al. | |
| 9,663,417 B2 | 5/2017 | Dakka et al. | |
| 2014/0212666 A1 | 7/2014 | Dakka et al. | |
| 2014/0315021 A1 | 10/2014 | Naert et al. | |
| 2015/0080546 A1* | 3/2015 | Dakka | C07C 51/265 528/305 |
| 2015/0099897 A1 | 4/2015 | Buchbinder et al. | |
| 2015/0361027 A1 | 12/2015 | Dakka et al. | |

FOREIGN PATENT DOCUMENTS

| | | |
|---|---|---|
| WO | 2000015597 A1 | 3/2000 |
| WO | 200575403 A1 | 8/2005 |
| WO | 2014117076 A1 | 7/2014 |
| WO | 2015112252 A1 | 7/2015 |
| WO | 2015191281 A1 | 12/2015 |

OTHER PUBLICATIONS

Tris(acetoacetonyl)cobalt 2015 (Year: 2015).*
Byron et al., "Effects of 3'- and 4'-substituents on the ionization constants of biphenyl-4-carboxylic acid and 4-aminobiphenyl", J. Chem. Soc., 1966, vol. 9, pp. 831-836.
Godwin, "Plasticizers", Applied Polymer Science 21st Century, ed. Craver and Carraher, Elsevier (2000), pp. 157-175.

* cited by examiner

SELECTIVE AEROBIC OXIDATION OF DIMETHYLBIPHENYLS

CROSS-REFERENCE TO RELATED APPLICATIONS

This application claims the benefit of U.S. Provisional Application No. 62/437,892, filed on Dec. 22, 2016, the entire contents of which are incorporated herein by reference.

This application also claims the benefit of related U.S. Provisional Application No. 62/437,823, filed on Dec. 22, 2016, the entire contents of which are incorporated herein by reference.

FIELD

Disclosed are processes for improving selective oxidation of dimethyl biphenyls in the presence of air by modifying various parameters to improve reaction rate and favor formation of methylbiphenyl mono-carboxylic acids.

BACKGROUND

Plasticizers are incorporated into a resin (usually a plastic or elastomer) to increase the flexibility, workability, or dispensability of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for 85% worldwide of PVC plasticizer usage in 2002.

It would be advantageous to develop a new generation of plasticizers with improved performance compared to phthalate esters.

SUMMARY

In one form is disclosed a process for selective oxidation of dimethyl-1,1'-biphenyl to form methyl-1,1'-biphenyl mono-carboxylic acid(s), comprising contacting a solution of dimethyl-1,1'-biphenyl in acetic acid solvent in the presence of a Co(II) acetate catalyst and air, and optionally (i) adding a co-solvent, or (ii) adding sodium or potassium acetate, and oxidizing the dimethyl-1,1'-biphenyl under time and temperature conditions sufficient to form one or more methyl-1,1'-biphenyl mono-carboxylic acid(s).

Advantageously, the selectivity for formation of methyl-1,1'-biphenyl mono-carboxylic acids is enhanced relative to the formation of other 1,1'-biphenyl oxygenates.

In another form, the process comprises adding the co-solvent, wherein the co-solvent is one that affects the acid strength of the solution, such as trifluorotoluene.

In some forms, the process comprises adding sodium acetate or potassium acetate, or can comprise adding one or more of Mn(II) acetate, Ni(II) acetate, Zn(II) acetate, Zr(IV) acetate, Fe(II) acetate.

In one form, the dimethyl-1,1'-biphenyl is provided in a mixture of dimethylbiphenyl isomers.

In yet another form, the process can further comprise limiting the total conversion to 55-70% when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates; or limiting the total conversion to 45-55% when the 3,3'-isomers of dimethylbiphenyl comprise between 10 and 30 wt % in the feed, so as to increase the overall yield of methyl-1,1'-biphenyl mono-carboxylic acids relative to other 1,1'-biphenyl oxygenates; or limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

Conveniently, the process is conducted such that the oxidizing temperature is from about 100° C. to about 150° C., or wherein the oxidizing temperature is from about 110° C. to about 150° C., or wherein the oxidizing temperature is from about 110° C. to about 130° C., or even wherein the oxidizing temperature starts at about ≥130° C. and is reduced to about 100° C. after reaction initiation.

In another form, the process further comprises adding Co(III)(acetylacetonate)$_3$, benzaldehyde, acetaldehyde or biphenyl-aldehydes as an initiator.

In another form, the catalyst concentration in the solution is from about 7.6 mM (450 ppm) to about 100 mM (6000 ppm), or the catalyst concentration in the solution is from about 23 mM (1350 ppm) to about 100 mM (6000 ppm).

In yet another form, the dimethyl-1,1'-biphenyl feed contains up to about 1 wt % of impurities that are known to inhibit free radical formation, including methylcyclohexyltoluenes and/or fluorenes.

In another form is disclosed a process for forming methylbiphenyl mono-esters, comprising selectively oxidizing dimethyl-1,1'-biphenyl to form methyl-1,1'-biphenyl mono-carboxylic acids, by contacting a solution of dimethyl-1,1'-biphenyl in acetic acid in the presence of a Co(II) acetate catalyst and air, and optionally (i) adding a co-solvent, or (ii) adding sodium or potassium acetate, and oxidizing the dimethyl-1,1'-biphenyl under time and temperature conditions sufficient to form one or more methyl-1,1'-biphenyl mono-carboxylic acid(s), and reacting the methyl-1,1'-biphenyl mono-carboxylic acids with $C_4$ to $C_{13}$ alcohols under esterification conditions.

Advantageously, the selectivity for formation of methyl-1,1'-biphenyl mono-carboxylic acids is enhanced relative to the formation of other 1,1'-biphenyl oxygenates.

In one form, the process comprises adding the co-solvent, wherein the co-solvent is one that affects the acid strength of the solution, such as trifluorotoluene.

In some forms, the process comprises adding sodium acetate or potassium acetate, and can even further comprise adding one or more of Mn(II) acetate, Ni(II) acetate, Zn(II) acetate, Zr(IV) acetate, Fe(II) acetate.

In another form, the dimethyl-1,1'-biphenyl is provided in a mixture of dimethylbiphenyl isomers.

In yet another form, the process can further comprise limiting the total conversion to 55-70% when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates; or limiting the total conversion to 45-55% when the 3,3'-isomers of dimethylbiphenyl comprise between 10 and 30 wt % in the feed, so as to increase the overall yield of methyl-1,1'-biphenyl mono-carboxylic acids relative to other 1,1'-biphenyl oxygenates; or limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

Conveniently, the process is conducted such that the oxidizing temperature is from about 100° C. to about 150° C., or wherein the oxidizing temperature is from about 110° C. to about 150° C., or wherein the oxidizing temperature is from about 110° C. to about 130° C., or even wherein the oxidizing temperature starts at about ≥130° C. and is reduced to about 100° C. after reaction initiation.

In another form, the process further comprises adding Co(III)(acetylacetonate)$_3$, benzaldehyde, acetaldehyde or biphenyl-aldehydes as an initiator.

In another form, the catalyst concentration in the solution is from about 7.6 mM (450 ppm) to about 100 mM (6000 ppm), or the catalyst concentration in the solution is from about 23 mM (1350 ppm) to about 100 mM (6000 ppm).

In yet another form, the dimethyl-1,1'-biphenyl feed contains up to about 1 wt % of impurities that are known to inhibit free radical formation, including methylcyclohexyl-toluenes and/or fluorenes.

In yet another form, the alcohols are OXO-alcohols.

BRIEF DESCRIPTION OF THE DRAWINGS

The present disclosure is susceptible to various modifications and alternative forms, specific exemplary implementations thereof have been shown in the drawings and are herein described in detail. It should be understood, however, that the description herein of specific exemplary implementations is not intended to limit the disclosure to the particular forms disclosed herein.

DETAILED DESCRIPTION

Figure 1:
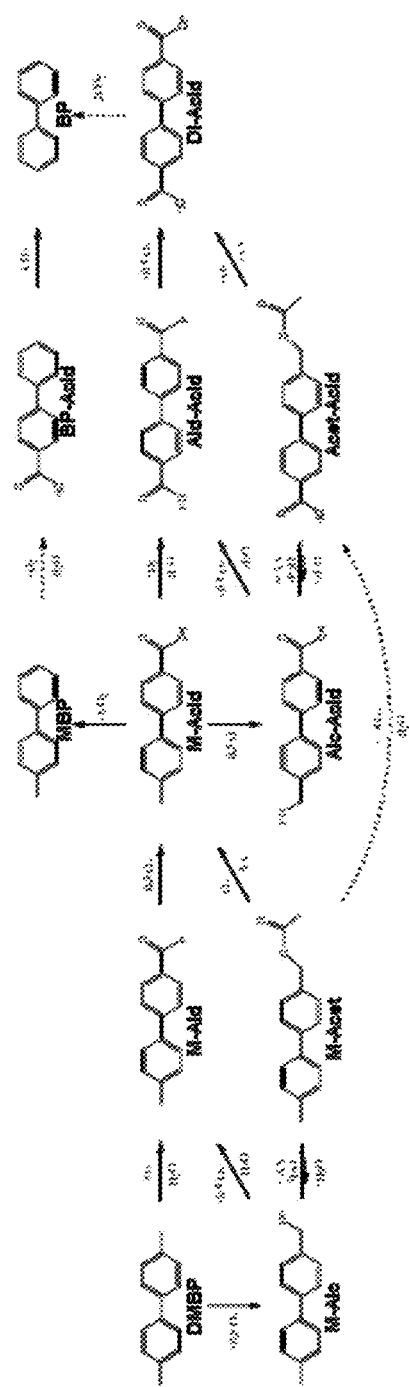
FIG. 1 shows a number of possible reaction pathways for oxidation of 4,4'-DMBP.

All numerical values within the detailed description and the claims herein are modified by "about" or "approximately" the indicated value, and take into account experimental error and variations that would be expected by a person having ordinary skill in the art.

There is an increased interest in developing new plasticizers which possess good plasticizer performance characteristics but are still competitive economically. The present disclosure is directed towards OXO-ester plasticizers, that can be made from low cost feeds and employ fewer manufacturing steps in order to meet economic targets.

Definitions

The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

A/an: The articles "a" and "an" as used herein mean one or more when applied to any feature in embodiments and implementations of the present invention described in the specification and claims. The use of "a" and "an" does not limit the meaning to a single feature unless such a limit is specifically stated. The term "a" or "an" entity refers to one or more of that entity. As such, the terms "a" (or "an"), "one or more" and "at least one" can be used interchangeably herein.

About: As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussion below regarding ranges and numerical data. All numerical values within the detailed description and the claims herein are modified by "about" the indicated value.

And/or: The term "and/or" placed between a first entity and a second entity means one of (1) the first entity, (2) the second entity, and (3) the first entity and the second entity. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of".

Comprising: In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. Any device or method or system described herein can be comprised of, can consist of, or can consist essentially of any one or more of the described elements.

Ranges: Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and about 200, but also to include individual sizes such as 2, 3, 4, etc. and sub-ranges such as 10 to 50, 20 to 100, etc. Similarly, it should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds). In the figures, like numerals denote like, or similar, structures and/or features; and each of the illustrated structures and/or features may not be discussed in detail herein with reference to the figures. Similarly, each structure and/or feature may not be explicitly labeled in the figures; and any structure and/or feature that is discussed herein with reference to the figures may be utilized with any other structure and/or feature without departing from the scope of the present disclosure.

The term dimethylbiphenyl (DMBP) refers to the starting compound of the presently described processes, which is 4,4'-dimethyl-1,1'-biphenyl having the following chemical structure:

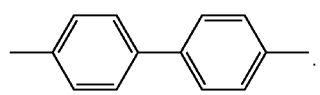

Other suitable starting isomers include 3,3'-dimethyl-1,1'-biphenyl and 3,4'-dimethyl-1,1'-biphenyl, which often occur in mixtures with 4,4'-dimethyl-1,1'-biphenyl. Additional suitable starting isomers include 2,2'-dimethyl-1,1'-biphenyl, 2,3'-dimethyl-1,1'-diphenyl, and 2,4'-dimethyl-1,1'-biphenyl. For convenience, the structures below are shown as the 4,4'-isomers, but it will be understood that the 3,3'-, 4,3'- and 3,4'-isomers, 2,2'-isomers, 2,3'- and 3,2'-isomers, and 2,4'- and 4,2'-isomers of these compounds are also covered by the general terminologies.

The term "M-Acid" refers to a mono-carboxylic acid of a DMBP molecule, in particular 4'-methyl-1,1'-biphenyl-4-carboxylic acid, a desired product of the present processes. The chemical structure of methyl-1,1'-biphenyl-carboxylic acid is:

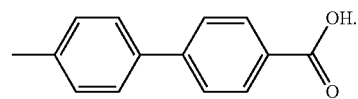 [SMILES: Cc1ccc(-c2ccc(C(=O)O)cc2)cc1]

The term "M-Ald" refers to a mono-aldehyde of a DMBP molecule, which has the following chemical structure:

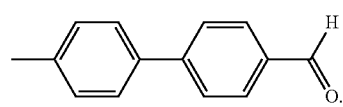

The term "M-Alc" refers to a mono-methylalcohol of a DMBP molecule, which has the following chemical structure:

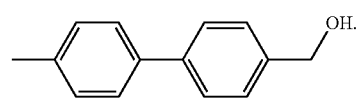

The term "M-Acet" refers to a mono-methylacetate of a DMBP molecule, which has the following chemical structure:

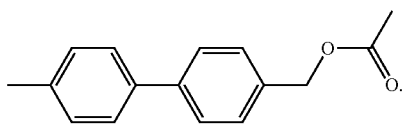 [SMILES: CC(=O)OCc1ccc(-c2ccc(C)cc2)cc1]

The term "Alc-Acid" refers to a biphenyl molecule having a methylalcohol substituent on one ring and an acid substituent on the other ring, which has the following chemical structure:

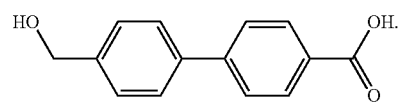 [SMILES: O=C(O)c1ccc(-c2ccc(CO)cc2)cc1]

The term "Ald-Acid" refers to a biphenyl molecule having an aldehyde substituent on one ring and an acid substituent on the other ring, which has the following chemical structure:

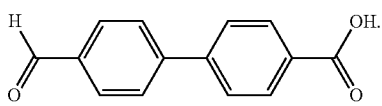 [SMILES: O=Cc1ccc(-c2ccc(C(=O)O)cc2)cc1]

The terms "Di-Acid" or "D-Acid" refers to a biphenyl molecule having carboxylic acid substituents on each ring, which has the following chemical structure.

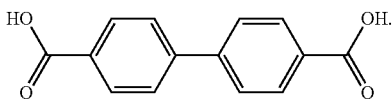

The term "Acet-Acid" refers to a biphenyl molecule having a methylacetate substituent on one ring and an acid substituent on the other ring, which has the following chemical structure:

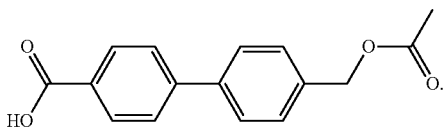 [SMILES: CC(=O)OCc1ccc(-c2ccc(C(=O)O)cc2)cc1]

The various biphenyl molecules described above which have oxygen-containing moieties on both phenyl groups are considered to be "over-oxidized" products.

An "OXO-ester" is a compound having at least one functional ester moiety within its structure derived from esterification of either an acid or alcohol compound with an OXO-alcohol or OXO-acid, respectively.

An "OXO-alcohol" is an organic alcohol, or mixture of organic alcohols, which is prepared by hydroformylating an olefin, followed by hydrogenation to form the alcohols. Typically, the olefin is formed by light olefin oligomerization over heterogenous acid catalysts, which olefins are readily available from refinery processing operations. The reaction results in mixtures of longer-chain, branched olefins, which subsequently form longer chain, branched alcohols, as described in U.S. Pat. No. 6,274,756, incorporated herein by reference in its entirety. The OXO-alcohols consist of multiple isomers of a given chain length due to the various isomeric olefins obtained in the oligomerization process, in tandem with the multiple isomeric possibilities of the hydroformylation step.

The purpose of the presently disclosed plasticizers is to replace the currently used, phthalate-based plasticizers with an alternative for the global general purpose plasticizer market. One potential route to new products is to use dimethylbiphenyl (DMBP) isomers. The DMBP molecules can be oxidized to produce many molecules. FIG. 1 shows some of the pathways that exist, the dashed arrows representing multiple reaction steps. The methods disclosed herein are specific for improved selectivity to the methyl-1,1'-biphenyl-carboxylic acids (mono-acids). The acid groups can be esterified with OXO-alcohols to produce esters and when the methyl and carboxylic acid groups are on adjacent rings in the 3- or 4-positions, the final esters have excellent plasticizer properties.

The M-Ald, M-Alc and M-Acet molecules are considered to be under-oxidized, but are relatively easily converted to the M-Acid. These under-oxidized molecules can be recycled into the oxidation reaction for conversion to M-Acids. In contrast, the Ald-Acid, Acet-Acid and Di-Acid molecules are considered to be over-oxidized, and coversion back to an M-Acid is more difficult. The processes of the present application explore ways of avoiding over-oxidation products in favor of either under-oxidized products or M-Acids.

There are many homogeneous processes for oxidation of alkylaromatics and most of them involve the full oxidation of all the alkyl groups to carboxylic acids; some examples include, toluene to benzoic acid, p-xylene to terephthalic acid, m-xylene to isophthalic acid, pseudocumene to trimellitic acid, and 2,6-dimethylnaphthalene to naphthalene-2,6-dicarboxylic acid. These oxidations utilize the cobalt, manganese, and bromide in various ratios in acetic acid. Other processes with ortho-substituted alkyl groups can be oxidized by heterogeneous catalyst to produce anhydrides; for example, o-xylene is oxidized to produce phthalic anhydride over vanadium supported on titanium oxide. The most closely related oxidations to this work involve methods to retain one of the methyl groups on the aromatic ring. One example is the oxidation of p-xylene top-toluic acid. Oxidation of p-xylene can be done selectively if desired, utilizing only cobalt as the catalyst. Production of terephthalic acid requires stronger oxidizing. The mixture of cobalt, manganese, and bromide is reported to provide Mn—Br as the strong oxidant in the catalytic cycle.

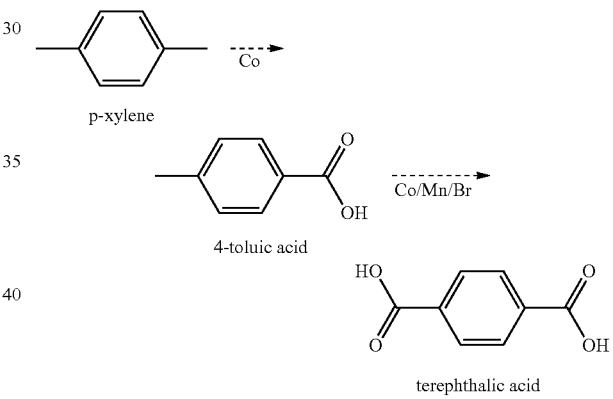

Oxidation of p-xylene to p-toluic acid is fairly easy because the first acid group that forms, deactivates the molecule toward further oxidation. However, the added aromatic ring in DMBP dampens the deactivation resulting in oxidation of the second methyl group to be fairly close in rate constant to the first.

Figure 2:
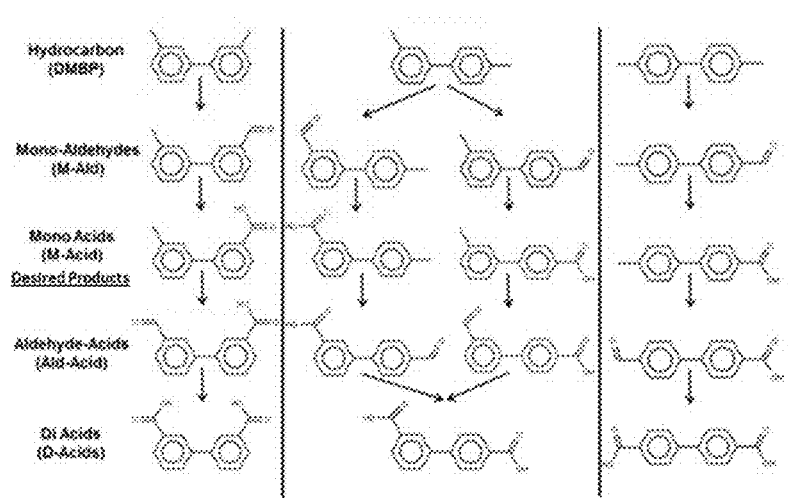
FIG. 2 shows potential oxidation products resulting from oxidation of biphenyl isomers mixtures.

DMBP is produced as a mixture of isomers and while the 2,3'- and 2,4'-isomers can be separated from the 3,3'-, 3,4'-, and 4,4'-DMBP isomers by distillation, additional separation of the latter is very expensive. Therefore, oxidation of a mixture of isomers is desirable, but it has been discovered that the selective oxidation of this mixture is also much more complex than any of the individual isomers. FIG. 2 illustrates some of the more abundant intermediates and isomers of intermediates of the reaction. The over-oxidized products, Ald-Acids and Di-Acids, represent yield loss because no market or feasible method of recovering them as M-Acids currently exists. Stopping the oxidation reaction at the M-Acids with high selectively for each isomer in a mixture is hampered by the fact that each isomer oxidizes at very different reaction rates. For example, pure 4,4'-DMBP oxidizes approximately 80 times faster than pure 3,3'-DMBP.

As shown in Table 1, at 50% conversion of a mixture of the three isomers, the 4,4'-isomer will typically reach 99% conversion before 3,3'-isomer reaches 20% conversion, and this leads to significant yields of unusable over-oxidized products.

TABLE 1

Yields of isomers at 50% conversion total DMBP

| Isomer | M-Ald | M-Acid | Ald-Acid | Di-Acid | % Isomer Conversion |
|---|---|---|---|---|---|
| 3,3'-DMBP | 6.6% | 14.3% | 0.4% | 0.6% | 20.4% |
| 3,4'-DMBP | 17.1% | 57.9% | 1.8% | 1.1% | 83.8% |
| 4,4'-DMBP | 7.2% | 71.5% | 4.1% | 1.6% | 99.7% |

Figure 3:
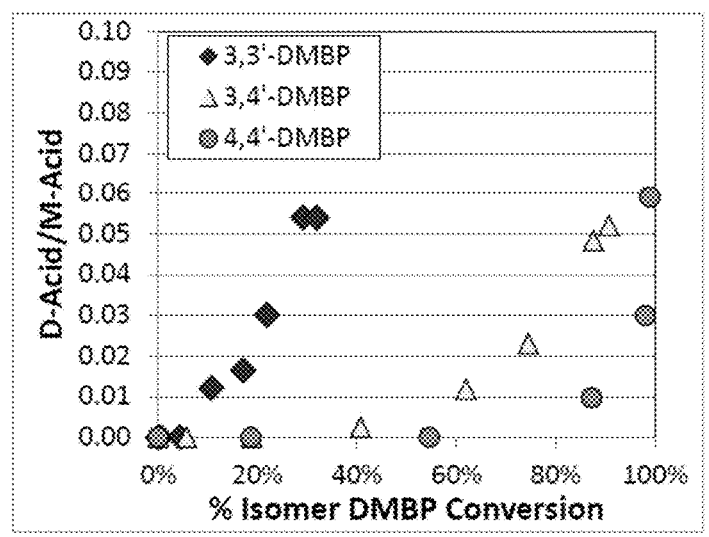
FIG. 3 shows the di-acid to mono-acid ratio as a function of conversion for the three DMBP isomers.

FIG. 3 illustrates the effect that the large difference in rates of reactivity between the isomers has on the ratios of Di-Acid and M-Acid for each isomer. The purification of M-Acid is also challenged by having a mixture of isomers. Taking melting point as an indicator of relative solubility (M.P. correlates inversely with solubility), the 3,3'-M-acid (M.P. 133.7° C.) has as very similar melting point as 4,4'-DMBP (M.P. 121.4° C.) and 4,4'-M-aldehyde (M.P. 105.9° C.), whereas the 3,4'-, 4,3'- and 4,4'-M-acids have melting points >185° C. It has been determined that this causes the 3,3'-M-acid isomer to be difficult to precipitate from the product mixture, resulting in 3,3'-M-acid to be recycled with the unreacted DMBP to the oxidation reactor where it becomes over-oxidized. The presence of soluble 3,3'-M-acid and other under-oxidized intermediates also enhances the solubility of the 3,4'- and 4,4'-M-acid isomers, pulling them into the recycle stream as well. The net result is a nearly entire yield loss of the 3,3'-isomer and low yields of the 3,4'- and 4,4'-M-acids.

In one form is disclosed a process for selective oxidation of dimethyl-1,1'-biphenyl to form methyl-1,1'-biphenyl mono-carboxylic acid(s), comprising contacting a solution of dimethyl-1,1'-biphenyl in acetic acid solvent in the presence of a Co(II) acetate catalyst and air, and optionally (i) adding a co-solvent, or (ii) adding sodium or potassium acetate, and oxidizing the dimethyl-1,1'-biphenyl under time and temperature conditions sufficient to form one or more methyl-1,1'-biphenyl mono-carboxylic acid(s).

In another form is disclosed a process for selective oxidation of dimethyl-1,1'-biphenyl to form methyl-1,1'-biphenyl mono-carboxylic acid(s), comprising contacting a solution of dimethyl-1,1'-biphenyl in acetic acid solvent in the presence of a Co(II) acetate catalyst and air, and optionally (i) adding a co-solvent, or (ii) adding sodium or potassium acetate, and oxidizing the dimethyl-1,1'-biphenyl under time and temperature conditions sufficient to form one or more methyl-1,1'-biphenyl mono-carboxylic acid(s), and reacting the methyl-1,1'-biphenyl mono-carboxylic acids with $C_4$ to $C_{13}$ alcohols under esterification conditions. Advantageously, the alcohols can be OXO-alcohols.

EXAMPLES

Figure 4:
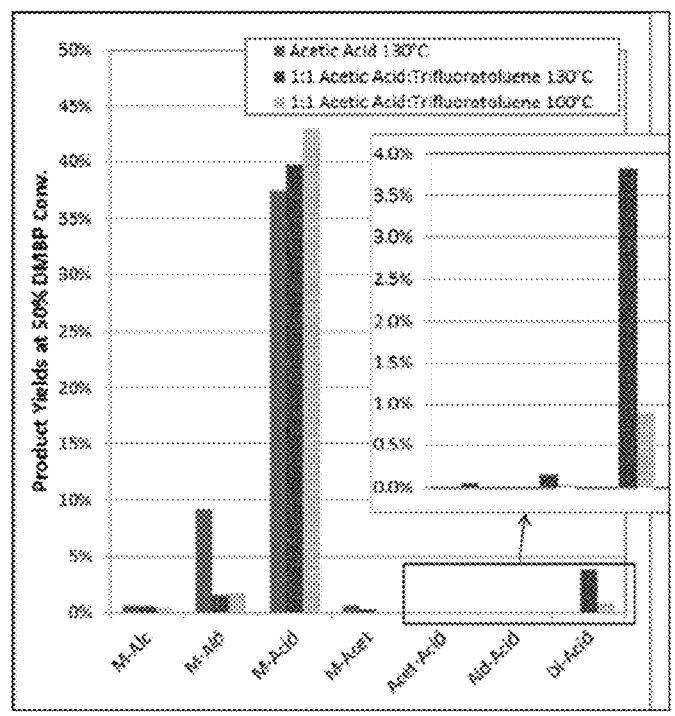
FIG. 4 shows a comparison of yield profiles for oxidation of 3,3'-DMBP, 3,4'-DMBP and 4,4'-DMBP.

Example 1: Oxidation of Mixed DMBP Isomers (3,3'-DMBP, 3,4'-DMBP, and 4,4'-DMBP) with a Co-Solvent A 300 ml Parr reactor was charged with 17.5 grams of a dimethylbiphenyl mixed isomer feed (with the following composition 56 wt % 3,3'-DMBP, 34 wt % 3,4'-DMBP, and 10 wt % 4,4'-DMBP), either 154 g of acetic acid or a 1:1 solution of acetic acid and trifluorotoluene, and Co(II) acetate to a concentration of 100 mM. The reactor was sealed and pressurized to 500 psig (3549 kPa-a) with nitrogen. The reactor was heated to 130° C. with a stir rate of 1200 rpm under 1500 cc/min $N_2$. When the temperature reached 130° C., $N_2$ was switched to air at the same flow rate. During the reaction, liquid samples were taken for GC analysis and the oxygen concentration in the gas effluent was measured. After the reaction, the air flow was switched to $N_2$, the reactor was cooled to room temperature then depressurized. In a third reaction the mixed solvent was utilized with a reaction at 100° C. The results were interpolated to 50% conversion and the product yields are shown in FIG. 4 for comparison. The M-Acid yield and M-Acid to M-Ald are drastically improved using the cosolvent. The decrease in reaction temperature allowed for the yield of over-oxidation products to be reduced by 76%. The results will improve the purification yields by minimizing the enhanced solubility that is observed when significant amounts of M-Ald are present in the products. In the reactions at 130° C., the oxidation rate was increased for all of the isomers allowing for higher throughput/lower residence time in the reactors, Table 2 below.

TABLE 2

| | 1$^{st}$ Order Rate Constants (s$^{-1}$) | | |
|---|---|---|---|
| Conditions | 3,3'-DMBP | 3,4'-DMBP | 4,4'-DMBP |
| Acetic Acid 130° C. | 2.1E−04 | 7.6E−04 | 1.4E−03 |
| 1:1 Acetic Acid:Trifluorotoluene 130° C. | 6.8E−04 | 1.3E−03 | 1.9E−03 |

It is believed that the reaction enhancements are a result of changes in acid strength of the solution. The acidity should decrease considerably resulting a decrease in available protons. It is an effective increase in pH of the solution. This change can also affect the redox potential of the reactants and intermediates. The affect allows the intermediate aldehydes to oxidize much easier, significantly increasing the selectivity of the reaction. It is additionally believed that other co-solvents which affect the acid strength of the acetic acid solvent would have similar effects. Halogenated aromatics and alkyl-aromatics are good examples, for they possess the following qualities: They are (1) stable to oxidizing conditions (i.e. possess no sp$^3$ hybridized C—H bonds), (2) more polar than acetic acid, and (3) less acidic than acetic acid.

Example 2: Oxidation of Mixed DMBP Isomers (2,X'-, 3,X'-, and 4,4'-DMBP)

Figure 5:
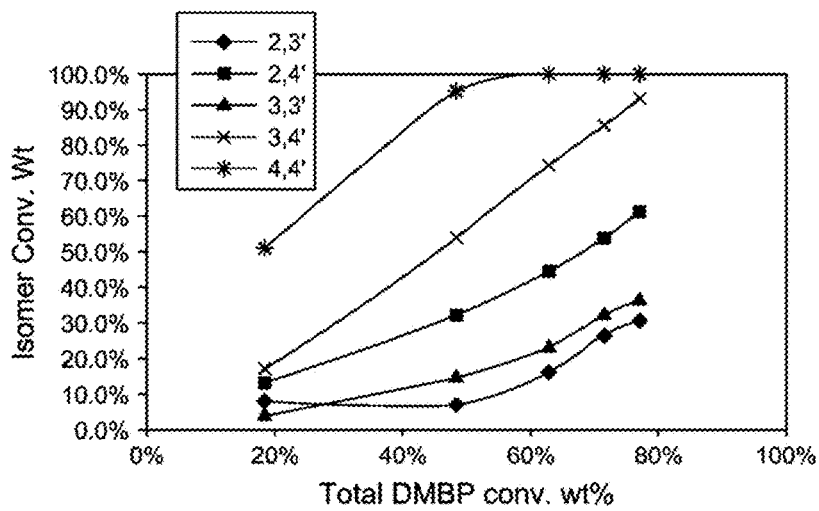
FIG. 5 shows the isomer conversion profile versus total DMBP conversion according to Example 2.

Oxidation was done batchwise. A 300 ml Parr reactor was charged with 30 grams of a dimethylbiphenyl mixed isomer feed (with the following composition 0.6 wt % 2,3'-DMBP, 1.9 wt % 2,4'-DMBP, 29 wt % 3,3'-DMBP, 52.8 wt % 3,4'-DMBP, and 15.7 wt % 4,4'-DMBP), 120 gms acetic acid, and 1500 ppm Co(II) acetate. The reactor was sealed and pressurized to 500 psig (3549 kPa-a) with nitrogen. The reactor was heated to 150° C. with a stir rate of 1200 rpm under 1500 cc/min $N_2$. When the temperature reached 150° C., $N_2$ was switched to air at the same flow rate. During the reaction, liquid samples were taken for GC analysis and the oxygen concentration in the gas effluent was measured. After 2 hours reaction time the air flow was switched to $N_2$, the reactor was cooled to room temperature then depressurized. The oxidation conversion/selectivity profile is shown in FIG. 5. This experiment indicates that mixtures of isomers can be oxidized to mixtures of M-Acids selectively and that the relative reaction rate by ring position is 4>3>2, and by isomer 4,4'>3,4'>2,4'>3,3'>2,3'

Example 3: Oxidation of Mixed DMBP Isomers Spiked with 1 wt % Methylcyclohexyl Toluene and 100 PPM Fluorene Oxidation was done batchwise. A 300 ml Parr reactor was charged with 30 grams of a dimethylbiphenyl mixed isomer feed (with the following composition 0.6 wt % 2,3'-DMBP, 1.9 wt % 2,4'-DMBP, 29 wt % 3,3'-DMBP, 52.8 wt % 3,4'-DMBP, and 15.7 wt % 4,4'-DMBP) spiked with 1 wt % methylcyclohexyl toluene (MCHT) and 100 ppm fluorene, 120 gms acetic acid, and 1500 ppm Co(II) acetate. The reactor was sealed and pressurized to 500 psig (3549 kPa-a) with nitrogen. The reactor was heated to 150° C. with a stir rate of 1200 rpm under 1500 cc/min $N_2$. When the temperature reached 150° C., $N_2$ was switched to air at the same flow rate. During the reaction liquid samples were taken for GC analysis and the oxygen concentration in the gas effluent was measured. After 2 hours reaction time the air flow was switched to $N_2$, the reactor was cooled to room temperature then depressurized. The oxidation conversion/selectivity profile for the spiked DMBP mixture of this example was compared with that for unspiked DMPB isomer mixture of Example 1. The the oxidation rate and acid selectivity were substantially unchanged when the mixed DMBP feed is contaminated with methylcyclohexyltoluene and/or fluorene, which inhibit free radical formation via a beta scission mechanism. This observation indicates that the catalytic system described is resistant to inhibition by phenolic radicals that would be expected to form from oxidation of MCHTs and fluorene followed by β-scission.

Example 4: Oxidation of Mixed DMBP Isomers (3,3'-, 3,4'-, and 4,4'-DMBP) with Other Metals A 300 ml Parr reactor was charged with 15 grams of a dimethylbiphenyl mixed isomer feed (with the following composition 25 wt % 3,3'-DMBP, 55 wt % 3,4'-DMBP, and 20 wt % 4,4'-DMBP), and 135 gms acetic acid. The type of metal acetate and its concentration that was added for each experiment is give in Table 3 below. The reactor was sealed and pressurized to 500 psig (3549 kPa-a) with nitrogen. The reactor was heated to 150° C. with a stir rate of 1200 rpm under 1500 cc/min $N_2$. When the temperature reached 150° C., $N_2$ was switched to air at the same flow rate. During the reaction, liquid samples were taken for GC analysis and the oxygen concentration in the gas effluent was measured. After the reaction, the air flow was switched to $N_2$, the reactor was cooled to room temperature then depressurized. The yields interpolated to 50% conversion are shown in Table 3 for comparison. The various metals or metal combinations shown were all able to successfully catalyze the oxidation of DMBP.

TABLE 3

| Total Metals (mM) | Metal Acetates (relative mol %) | Yields at 50% conversion of DMBP ||||||| 
|---|---|---|---|---|---|---|---|---|
| | | M-Alc | M-Ald | M-Acid | M-Acet | Ald-Acid | Di-Acid | Conv % |
| 15.1 | 90% Co(II):10% Mn(II) | 0.7% | 13.2% | 26.4% | 6.2% | 0.9% | 0.3% | 50.0% |
| 30.2 | 100% Mn(II) | 0.5% | 7.8% | 27.1% | 8.2% | 0.9% | 1.9% | 50.0% |
| 15.1 | 50% Co(II):50% Ni(II) | 1.5% | 14.0% | 24.5% | 5.5% | 0.6% | 0.4% | 50.0% |
| 15.1 | 50% Co(II):50% Zn(II) | 1.4% | 13.5% | 24.7% | 6.2% | 0.7% | 0.4% | 50.0% |
| 15.1 | 50% Co(II):50% Zr(II) | 1.3% | 16.3% | 25.2% | 2.4% | 0.9% | 0.6% | 50.0% |
| 15.1 | 50% Co(II):50% Fe(II) | 1.5% | 12.1% | 16.6% | 6.6% | 0.2% | 0.1% | 39.0% |

Example 5-7 were conducted under the conditions as set forth in Example 1 above without co-solvent, except as noted. These examples were conducted to explore the results in variations in reaction temperatures, initiators and catalysts.

Example 5: Comparison of Oxidation of DMBP Isomers with Varying Reaction Temperatures The overall yield of the reaction can be increased by decreasing the temperature of the reaction. Table 4 compares data from single-pass experiments that only vary from each other in temperature (20 wt % total DMBP and 23 mM Co). The yield of undesirable overoxidized, Acet-Acid, Ald-Acid and Di-Acid, products is smaller at lower temperatures; at 130° C., the yield loss through formation of these overoxidized products is 23% less (2.0% compared to 2.6%) than at 150° C. The final process with isolated M-Acid and recycled under-oxidized products will have a much lower yield loss if operated at a lower temperature.

TABLE 4

| | Total Product Yields |||||||||
|---|---|---|---|---|---|---|---|---|---|
| Temp (° C.) | M-Alc | M-Ald | M-Acid | M-Acet | Acet-Acid | Ald-Acid | Di-Acid | % Conv | Total Overoxidized |
| 130 | 0.8% | 6.4% | 34.6% | 3.1% | 0.2% | 0.8% | 1.0% | 50.0% | 2.0% |
| 150 | 0.9% | 8.4% | 32.7% | 2.1% | 0.2% | 1.0% | 1.4% | 50.0% | 2.6% |

Another example showed that that there is a an additional increase in the mono-acid/mono-aldehyde ratio as temperature is decreased to 110° C. Oxidizing pure 4,4'-DMBP at 150° C., 130° C., and 110° C. the M-Acid/M-Ald ratio increased from 0.76 to 1.0, as demonstrated in Table 5

TABLE 5

| | | | Total Product Yields | | | | | | |
|---|---|---|---|---|---|---|---|---|---|
| Temp (° C.) | M-Alc | M-Ald | M-Acid | M-Acet | Ald-Acid | Di-Acid | % Conv | Total Over-oxidized | M-Acid/M-Ald |
| 150 | 3.29% | 22.73% | 17.34% | 10.36% | 1.38% | 0.49% | 60% | 1.86% | 0.76 |
| 130 | 5.68% | 23.14% | 19.26% | 3.53% | 0.77% | 0.00% | 60% | 0.77% | 0.83 |
| 110 | 3.07% | 22.81% | 22.74% | 4.94% | 1.11% | 0.00% | 60% | 1.11% | 1.00 |

Figure 6:
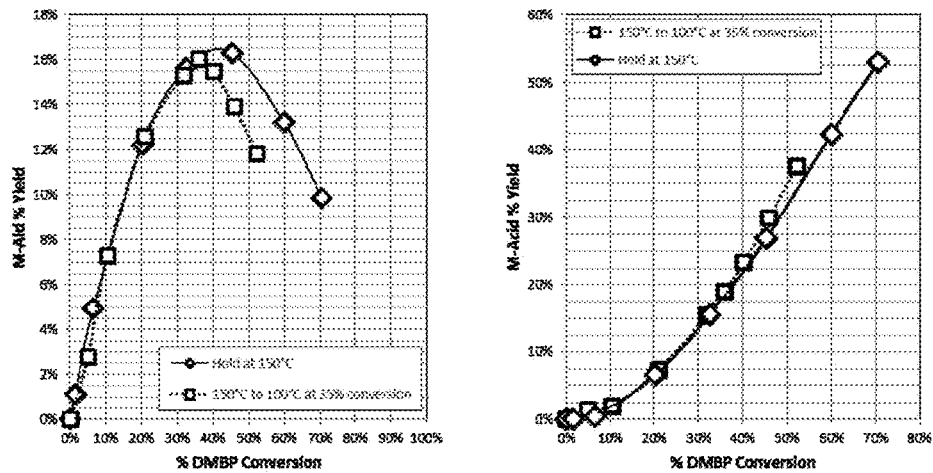
FIG. 6 demonstrates the advantages of a two-step temperature oxidation of DMBP to M-Ald relative to M-Acid.

M-Ald can be oxidized more efficiently at low temperature compared to M-Acid. A two-step reaction where the reaction is initiated at a higher temperature and reduced to a lower temperature reduces the M-Ald yield and increases M-Acid yield. In addition to increasing the M-Acid yield directly, the reduced M-Ald yield makes it easier to purify and isolate the desired M-Acids. As shown in FIG. 6, compared to holding the temperature at 150° C. for the entire reaction, dropping the temperature the temperature to 100° C. at 35% conversion allow the yields at 50% conversion to change in a beneficial way: the M-Ald yield decreased from 15.5% to 12.5%, while the M-Acid yield increased from 32 to 35%.

Example 6: Effects of Various Initiators on DMBP Oxidation

Figure 7:
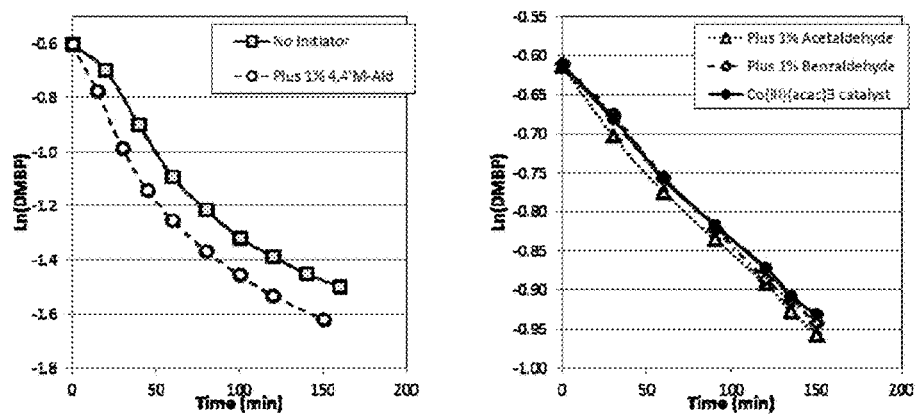
FIG. 7 demonstrates the effects of utilizing various initiators for the oxidation of DMBP.

The reaction can be initiated using Co(III)(acetylacetonate)$_3$ (Cobalt AcAc) or aldehydes such as benzaldehyde, acetaldehyde, or M-Ald intermediates. The initiation allows the reaction to proceed at time zero at close to the steady state rate observed in reactions without initiators. M-Ald will be present in the under-oxidized products that can be recycled back to the feed and can thus act as an initiators in the process. In FIG. 7 below, 4,4'-M-Ald can be seen as an initiator in the oxidation of a mixed isomer DMBP feed (23 mM Co and 150° C.). The non-initiated reaction takes about 35 minutes to reach the maximum reaction rate that is observed almost immediately in the initiated reaction. On the right, oxidation of 10 wt % of the pure 3,3'-DMBP isomer at 150° C. with 15 mM Co takes hours before autoxidation and reaction initiation occurs. Under the same conditions with added initiators, such as Co(III)(acetylacetonate)$_3$ (as the source of Co) or aldehydes such as benzaldehyde and acetaldehyde, this isomer can be oxidized without delay.

Example 7: Effects of Varying Catalyst Concentrations on DMBP Oxidation

Figure 8:
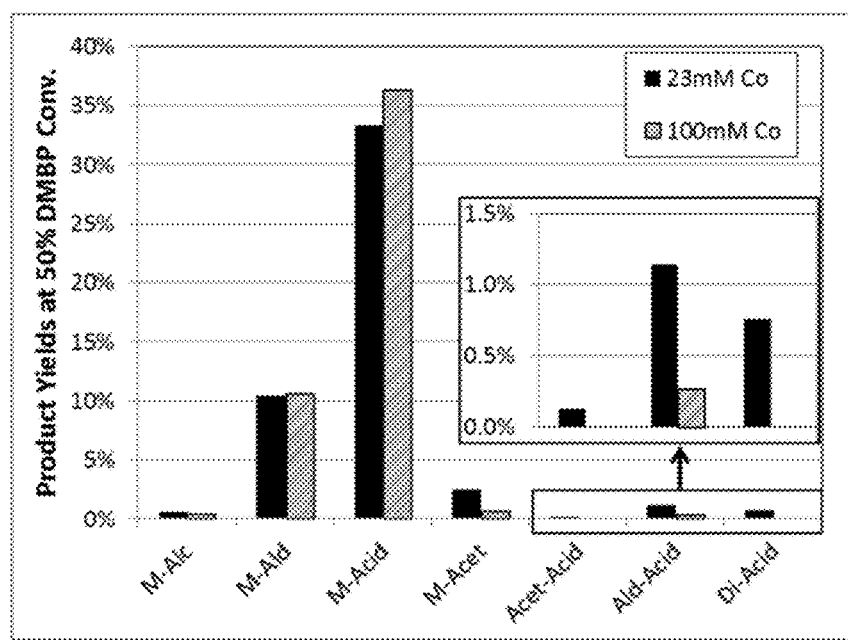
FIG. 8 demonstrates the changes in product yields as a result of different catalyst concentrations.

Very high catalyst concentrations can be used to achieve increased M-Acid yield and decrease side-reactions that produced undesired by-products and over-oxidation products. This could be caused by an increase in rate of cobalt catalyzed reactions relative to radical C—H bond attack, which is more strongly oxidizing. The reaction can benefit from higher concentrations of all catalysts, including Cobalt acetate, Cobalt AcAc, Mn, and mixed metal Co—X (where X is Fe, Ni, Mn, Zr, Zn, etc.). FIG. 8 shows the increase in selectivity of M-Acid and decrease in selectivity of M-Alc, M-Acet, Acet-Acid, Ald-Acid, and Di-Acid that results from the increase in catalyst concentration from 23 mM to 100 mM.

Figure 9:
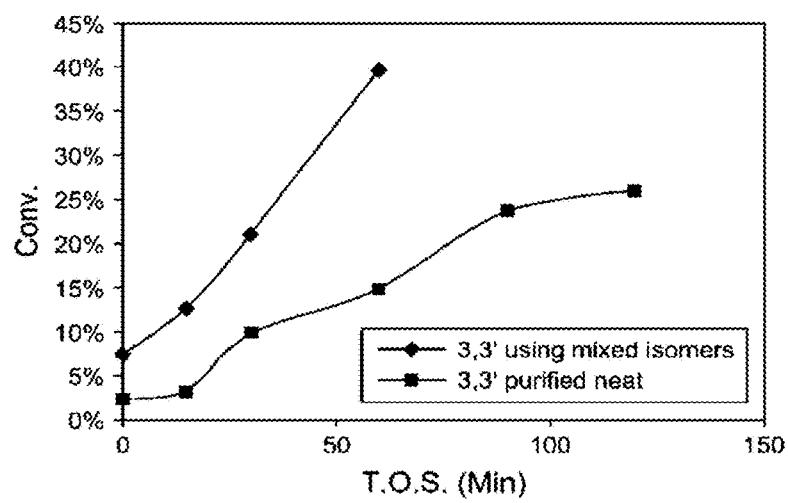
FIG. 9 shows that conversion of 3,3'-DMBP is much slower in the absence of other isomers.
Figure 10:
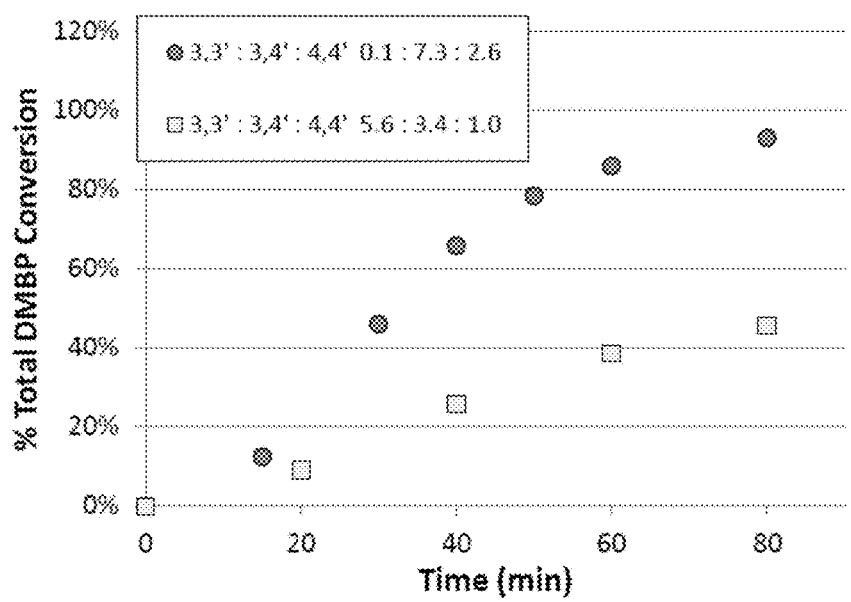
FIG. 10 shows that decreasing the concentration of 3,3'-DMBP relative to the other isomers of DMBP increases the overall reaction rate.

Example 8: Comparison of Oxidation of DMBP Isomers with Varying Concentrations of 3,3'-DMBP Oxidation of the 3,3'-DMBP isomer is very sluggish in the absence of an initiator. Having a 4,4'-DMBP and/or 3,4'-DMBP in the feed increases the reaction rate, allowing 3,3'-DMBP oxidation to proceed uninhibited. In FIG. 9, oxidation rates of 3,3'-DMBP alone and in the presence of other isomers was compared. The reaction conditions were identical (20 wt % total DMBP, 150° C., and 25 mM Co) except for the DMBP composition being varied from pure 3,3'-DMBP to a mixed ratio of 25:55:20 for 3,3':3,4':4,4'-DMBP One method of increasing the overall rate of the reaction is to decrease the concentration of 3,3'-DMBP in the feed. As shown in FIG. 10, under otherwise identical conditions (10 wt % total DMBP, 150° C., and 1340 ppmW Co), oxidizing feeds having a very high concentration of 4-position methyl groups allows the reaction to proceed at higher rates.

The overall yield of M-Acid increases when 3,4'-DMBP and 4,4'-DMBP are very high in concentration in the feed. As shown in the table below, at otherwise similar conditions, (10 wt % total DMBP, 150° C., and 1340 ppmW Co) when the feed composition has very little 3,3'-DMBP and the process is run at similar conversion, the loss of product to the undesirable over-oxidized Acet-Acid, Ald-Acid and Di-Acid products is decreased from 2% to 0.5%, as demonstrated in Table 6 below.

TABLE 6

| Relative wt % in feed | | | Total Product Yields | | | | | | | | |
|---|---|---|---|---|---|---|---|---|---|---|---|
| 3,3'-DMBP | 3,4'-DMBP | 4,4'-DMBP | M-Alc | M-Ald | M-Acid | M-Acet | Acet-Acid | Ald-Acid | Di-Acid | % Conv | Total Over-oxidized |
| 56.1 | 33.9 | 10.0 | 0.5% | 10.4% | 33.3% | 2.4% | 0.1% | 1.1% | 0.8% | 50.0% | 2.0% |
| 0.8 | 73.1 | 26.1 | 2.0% | 24.5% | 20.4% | 2.6% | 0.0% | 0.4% | 0.1% | 50.0% | 0.5% |

The final yield of M-Acid from the 3,4'-DMBP and 4,4'-DMBP isomers increases when more 3,3'-DMBP is present in the feed. The data tables below, Tables 7 and 8, shows that when similar conversions of the individual isomers are compared, for example in Table 7, 82.6% and 84.4% conversion occurred in the two different experiments, the yield of undesirable over-oxidized Acet-Acid, Ald-Acid and Di-Acid products increased from 2.7 to 4.5% when the 3,3'-DMBP was not present in the feed.

TABLE 7

| Relative wt % in feed | | | Yield of 3,4'-isomers | | | | | | | | |
|---|---|---|---|---|---|---|---|---|---|---|---|
| 3,3'-DMBP | 3,4'-DMBP | 4,4'-DMBP | M-Alc | M-Ald | M-Acid | M-Acet | Acet-Acid | Ald-Acid | Di-Acid | % Conv | Total Over-oxidized |
| 56.1 | 33.9 | 10.0 | 0.7% | 17.5% | 54.8% | 3.8% | 0.1% | 1.6% | 0.97% | 82.6% | 2.7% |
| 0.8 | 73.1 | 26.1 | 0.8% | 22.8% | 55.4% | 3.2% | 0.3% | 2.4% | 1.8% | 84.4% | 4.5% |

TABLE 8

| Relative wt % in feed | | | Yield of 4,4'-isomers | | | | | | | | |
|---|---|---|---|---|---|---|---|---|---|---|---|
| 3,3'-DMBP | 3,4'-DMBP | 4,4'-DMBP | M-Alc | M-Ald | M-Acid | M-Acet | Acet-Acid | Ald-Acid | Di-Acid | % Conv | Total Over-oxidized |
| 56.1 | 33.9 | 10.0 | 0.4% | 8.0% | 69.5% | 2.2% | 0.7% | 3.8% | 1.4% | 99.6% | 5.9% |
| 0.8 | 73.1 | 26.1 | 0.1% | 10.6% | 70.0% | 1.8% | 1.6% | 6.3% | 4.6% | 99.5% | 12.5% |

From the totality of the data, it has been determined that limiting the total conversion to 55-70% when the 3,3'-isomers of dimethylbiphenyl comprise less than 10 wt % in the feed increases the overall yield of methyl-1,1'-biphenyl mono-carboxylic acids relative to other 1,1'-biphenyl oxygenates, and that limiting the total conversion to 45-55% when the 3,3'-isomers of dimethylbiphenyl comprise between 10 and 30 wt % in the feed increases the overall yield of methyl-1,1'-biphenyl mono-carboxylic acids relative to other 1,1'-biphenyl oxygenates, and that limiting the total conversion to 30-45% when the 3,3'-isomers of dimethylbiphenyl comprise between 30 and 80 wt % in the feed increases the overall yield of methyl-1,1'-biphenyl mono-carboxylic acids relative to other 1,1'-biphenyl oxygenates.

Further illustrative, non-exclusive examples of systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

PCT/EP Clauses:

1. A process for selective oxidation of dimethyl-1,1'-biphenyl to form methyl-1,1'-biphenyl mono-carboxylic acid(s), comprising contacting a solution of dimethyl-1,1'-biphenyl in acetic acid solvent in the presence of a Co(II) acetate catalyst and air, and optionally (i) adding a co-solvent, or (ii) adding sodium or potassium acetate, and oxidizing the dimethyl-1,1'-biphenyl under time and temperature conditions sufficient to form one or more methyl-1,1'-biphenyl mono-carboxylic acid(s).

2. The process of paragraph PCT1, wherein the selectivity for formation of methyl-1,1'-biphenyl mono-carboxylic acids is enhanced relative to the formation of other 1,1'-biphenyl oxygenates.

3. The process of paragraph PCT1 or PCT2, comprising adding the co-solvent, wherein the co-solvent is one that affects the acid strength of the solution, such as trifluorotoluene.

4. The process of paragraph PCT1 or PCT2, comprising adding sodium acetate or potassium acetate, or adding one or more of Mn(II) acetate, Ni(II) acetate, Zn(II) acetate, Zr(IV) acetate, Fe(II) acetate.

5. The process of any of paragraphs PCT1 to PCT4, wherein the dimethyl-1,1'-biphenyl is provided in a mixture of dimethylbiphenyl isomers.

6. The process of paragraph PCT5, further comprising limiting the total conversion to 55-70% when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates; or limiting the total conversion to 45-55% when the 3,3'-isomers of dimethylbiphenyl comprise between 10 and 30 wt % in the feed, so as to increase the overall yield of methyl-1,1'-biphenyl mono-carboxylic acids relative to other 1,1'-biphenyl oxygenates; or limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

7. The process of any of paragraphs PCT1 to PCT6, wherein the oxidizing temperature is from 100° C. to 150° C., or wherein the oxidizing temperature is from 110° C. to 150° C., or wherein the oxidizing temperature is from 110° C. to 130° C., or even wherein the oxidizing temperature starts at ≥130° C. and is reduced to 100° C. after reaction initiation.

8. The process of any of paragraphs PCT1 to PCT7, further comprising adding Co(III)(acetylacetonate)$_3$, benzaldehyde, acetaldehyde or biphenyl-aldehydes as an initiator.

9. The process of any of paragraphs PCT1 to PCT8, wherein the catalyst concentration in the solution is from 7.6 mM (450 ppm) to 100 mM (6000 ppm), or the catalyst concentration in the solution is from 23 mM (1350 ppm) to 100 mM (6000 ppm).

10. The process of any of paragraphs PCT1 to PCT9, wherein the dimethyl-1,1'-biphenyl feed contains up to 1 wt % of impurities that are known to inhibit free radical formation, including methylcyclohexyltoluenes and/or fluorenes.

11. A process for forming methylbiphenyl mono-esters, comprising selectively oxidizing dimethyl-1,1'-biphenyl to form methyl-1,1'-biphenyl mono-carboxylic acids, by contacting a solution of dimethyl-1,1'-biphenyl in acetic acid in the presence of a Co(II) acetate catalyst and air, and optionally (i) adding a co-solvent, or (ii) adding sodium or potassium acetate, and oxidizing the dimethyl-1,1'-biphenyl under time and temperature conditions sufficient to form one or more methyl-1,1'-biphenyl mono-carboxylic acid(s), and reacting the methyl-1,1'-biphenyl mono-carboxylic acids with $C_4$ to $C_{13}$ alcohols under esterification conditions.

12. The process of paragraph PCT11, wherein the selectivity for formation of methyl-1,1'-biphenyl mono-carboxylic acids is enhanced relative to the formation of other 1,1'-biphenyl oxygenates.

13. The process of paragraph PCT11 or PCT12, comprising adding the co-solvent, wherein the co-solvent is one that affects the acid strength of the solution, such as trifluorotoluene.

14. The process of paragraph PCT11 or PCT12, comprising adding sodium acetate or potassium acetate, or adding one or more of Mn(II) acetate, Ni(II) acetate, Zn(II) acetate, Zr(IV) acetate, Fe(II) acetate.

15. The process of any of paragraphs PCT11 to PCT14, wherein the dimethyl-1,1'-biphenyl is provided in a mixture of dimethylbiphenyl isomers.

16. The process of paragraph PCT15, further comprising limiting the total conversion to 55-70% when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates; or limiting the total conversion to 45-55% when the 3,3'-isomers of dimethylbiphenyl comprise between 10 and 30 wt % in the feed, so as to increase the overall yield of methyl-1,1'-biphenyl mono-carboxylic acids relative to other 1,1'-biphenyl oxygenates; or limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

17. The process of any of paragraphs PCT11 to PCT16, wherein the oxidizing temperature is from 100° C. to 150° C., or wherein the oxidizing temperature is from 110° C. to 150° C., or wherein the oxidizing temperature is from 110° C. to 130° C., or even wherein the oxidizing temperature starts at ≥130° C. and is reduced to 100° C. after reaction initiation.

18. The process of any of paragraphs PCT11 to PCT17, further comprising adding Co(III)(acetylacetonate)$_3$, benzaldehyde, acetaldehyde or biphenyl-aldehydes as an initiator.

19. The process of any of paragraphs PCT11 to PCT18, wherein the catalyst concentration in the solution is from 7.6 mM (450 ppm) to 100 mM (6000 ppm), or the catalyst concentration in the solution is from 23 mM (1350 ppm) to 100 mM (6000 ppm).

20. The process of any of paragraphs PCT11 to PCT19, wherein the dimethyl-1,1'-biphenyl feed contains up to 1 wt % of impurities that are known to inhibit free radical formation, including methylcyclohexyltoluenes and/or fluorenes.

21. The process of any of paragraphs PCT11 to PCT20, wherein the alcohols are OXO-alcohols.

INDUSTRIAL APPLICABILITY

The systems and methods disclosed herein are applicable to the chemical industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A process for selective oxidation of dimethyl-1,1'-biphenyl to form methyl-1,1'-biphenyl mono-carboxylic acid(s), comprising:
    contacting a solution of dimethylbiphenyl isomers, including dimethyl-1,1'-biphenyl, in acetic acid solvent in the presence of a Co(II) acetate catalyst and air, and optionally:
    (i) adding a co-solvent, or
    (ii) adding sodium or potassium acetate, and
    oxidizing the dimethyl-1,1'-biphenyl under time and temperature conditions sufficient to form one or more methyl-1,1'-biphenyl mono-carboxylic acid(s), the process further comprising limiting the total conversion to 55-70% when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates.

2. The process of claim 1, wherein the selectivity for formation of methyl-1,1'-biphenyl mono-carboxylic acids is enhanced relative to the formation of other 1,1'-biphenyl oxygenates.

3. The process of claim 1, comprising adding the co-solvent, wherein the co-solvent is one that affects the acid strength of the solution.

4. The process of claim 3, wherein the co-solvent is trifluorotoluene.

5. The process of claim 1, comprising adding sodium acetate or potassium acetate.

6. The process of claim 1, further comprising adding one or more of Mn(II) acetate, Ni(II) acetate, Zn(II) acetate, Zr(IV) acetate, Fe(II) acetate.

7. The process of claim 1, further comprising limiting the total conversion to 45-55% when the 3,3'-isomers of dimethylbiphenyl comprise between 10 and 30 wt % in the feed, so as to increase the overall yield of methyl-1,1'-biphenyl mono-carboxylic acids relative to other 1,1'-biphenyl oxygenates.

8. The process of claim 1, further comprising limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

9. The process of claim 1, wherein the oxidizing temperature is from about 100° C. to about 150° C.

10. The process of claim 9, wherein the oxidizing temperature is from about 110° C. to about 150° C.

11. The process of claim 9, wherein the oxidizing temperature is from about 110° C. to about 130° C.

12. The process of claim 9, wherein the oxidizing temperature starts at about ≥130° C. and is reduced to about 100° C. after reaction initiation.

13. The process of claim 1, further comprising adding Co(III)(acetylacetonate)$_3$, benzaldehyde, acetaldehyde or biphenyl-aldehydes as an initiator.

14. The process of claim 1, wherein the catalyst concentration in the solution is from about 7.6 mM (450 ppm) to about 100 mM (6000 ppm).

15. The process of claim 1, wherein the catalyst concentration in the solution is from about 23 mM (1350 ppm) to about 100 mM (6000 ppm).

16. The process of claim 1, wherein the dimethyl-1,1'-biphenyl feed contains up to about 1 wt % of impurities that are known to inhibit free radical formation, including methylcyclohexyltoluenes and/or fluorenes.

17. A process for forming methylbiphenyl mono-esters, comprising:
 selectively oxidizing dimethyl-1,1'-biphenyl to form methyl-1,1'-biphenyl mono-carboxylic acids, by contacting a solution of dimethylbiphenyl isomers, including dimethyl-1,1'-biphenyl, in acetic acid in the presence of a Co(II) acetate catalyst and air, and optionally:
 (i) adding a co-solvent, or
 (ii) adding sodium or potassium acetate, and
 oxidizing the dimethyl-1,1'-biphenyl under time and temperature conditions sufficient to form one or more methyl-1,1'-biphenyl mono-carboxylic acid(s); and
 reacting the methyl-1,1'-biphenyl mono-carboxylic acids with $C_4$ to $C_{13}$ alcohols under esterification conditions, the process further comprising limiting the total conversion to 45-55% when the 3,3'-isomers of dimethyl-biphenyl comprise between 10 and 30 wt % in the feed, so as to increase the overall yield of methyl-1,1'-biphenyl mono-carboxylic acids relative to other 1,1'-biphenyl oxygenates.

18. The process of claim 17, wherein the selectivity for formation of methyl-1,1'-biphenyl mono-carboxylic acids is enhanced relative to the formation of other 1,1'-biphenyl oxygenates.

19. The process of claim 17, comprising adding the co-solvent, wherein the co-solvent is one that affects the acid strength of the solution.

20. The process of claim 17, wherein the co-solvent is trifluorotoluene.

21. The process of claim 17, comprising adding one of sodium acetate or potassium acetate.

22. The process of claim 17, further comprising adding one or more of Mn(II) acetate, Ni(II) acetate, Zn(II) acetate, Zr(IV) acetate, Fe(II) acetate.

23. The process of claim 17, further comprising limiting the total conversion to 55-70% when the 3,3'-isomers of dimethylbiphenyl comprise less than 10 wt % in the feed, so as to increase the overall yield of methyl-1,1'-biphenyl mono-carboxylic acids relative to other 1,1'-biphenyl oxygenates.

24. The process of claim 17, further comprising limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

25. The process of claim 17, wherein the oxidizing temperature is from about 100° C. to about 150° C.

26. The process of claim 25, wherein the oxidizing temperature is from about 110° C. to about 150° C.

27. The process of claim 25, wherein the oxidizing temperature is from about 110° C. to about 130° C.

28. The process of claim 25, wherein the oxidizing temperature starts at about ≥130° C. and is reduced to about 100° C. after reaction initiation.

29. The process of claim 17, further comprising adding Co(III)(acetylacetonate)$_3$, benzaldehyde, acetaldehyde or biphenyl-aldehydes as the initiator.

30. The process of claim 17, wherein the catalyst concentration in the solution is from about 7.6 mM (450 ppm) to about 100 mM (6000 ppm).

31. The process of claim 30, wherein the catalyst concentration in the solution is from about 23 mM (1350 ppm) to about 100 mM (6000 ppm).

32. The process of claim 17, wherein the dimethyl-1,1'-biphenyl feed contains up to about 1 wt % of impurities that are known to inhibit free radical formation, including methylcyclohexyltoluenes and/or fluorenes.

33. The process of claim 17, wherein the alcohols are OXO-alcohols.

34. A process for selective oxidation of dimethyl-1,1'-biphenyl to form methyl-1,1'-biphenyl mono-carboxylic acid(s), comprising:
 contacting a solution of dimethylbiphenyl isomers, including dimethyl-1,1'-biphenyl, in acetic acid solvent in the presence of a Co(II) acetate catalyst and air, and optionally:
 (i) adding a co-solvent, or
 (ii) adding sodium or potassium acetate, and
 oxidizing the dimethyl-1,1'-biphenyl under time and temperature conditions sufficient to form one or more methyl-1,1'-biphenyl mono-carboxylic acid(s), the process further comprising limiting the total conversion to 30-45% when the 3,3'-isomers of dimethylbiphenyl comprise between 30 and 80 wt % in the feed, so as to increase the overall yield of methyl-1,1'-biphenyl mono-carboxylic acids relative to other 1,1'-biphenyl oxygenates.

* * * * *